United States Patent [19]

Munteanu

[11] Patent Number: 4,917,301
[45] Date of Patent: Apr. 17, 1990

[54] CONTAINER WITH MICROPOROUS MEMBRANE FOR DISPENSING VAPOR FROM VOLATILE LIQUID

[75] Inventor: Marina A. Munteanu, New York, N.Y.

[73] Assignee: International Flavors & Fragrances, Inc., New York, N.Y.

[21] Appl. No.: 271,623

[22] Filed: Nov. 15, 1988

[51] Int. Cl.$^4$ .............................................. A61L 9/04
[52] U.S. Cl. ...................................... 239/43; 239/45; 239/57
[58] Field of Search ................ 239/34, 37, 43, 45, 239/57

[56] References Cited

U.S. PATENT DOCUMENTS

| | | | |
|---|---|---|---|
| 1,129,897 | 3/1915 | Owen, Jr. | 239/45 |
| 1,944,375 | 1/1934 | Schneider | 239/43 |
| 2,219,959 | 10/1940 | Laidley | 239/43 |
| 2,443,139 | 6/1948 | Krause | 239/43 |
| 2,766,069 | 10/1956 | Tennyson | 239/43 |
| 3,169,705 | 2/1965 | Geiger | 239/43 |
| 3,727,840 | 4/1973 | Nigro | 239/43 |
| 3,790,081 | 2/1974 | Thornton | 239/57 |
| 4,413,779 | 11/1983 | Santini | 239/45 |

FOREIGN PATENT DOCUMENTS 355880 7/1922 Fed. Rep. of Germany ........ 239/37

Primary Examiner—Andres Kashnikow
Assistant Examiner—Michael J. Forman
Attorney, Agent, or Firm—Brooks Haidt Haffner & Delahunty

[57] ABSTRACT

Volatile substances such as fragrances, perfumes, deodorizers, room freshener compositions and the like are dispensed in vapor phase from a container holding the substance in liquid phase at room temperature under atmospheric pressure. The container has a window covered with a microporous membrane with an active structure formed from a material having a critical surface tension that is below the surface tension of the liquid substance. The active membrane material has a critical surface tension that is below 22 dynes/cm and preferably below 20 dynes/cm while the surface tension of the liquid is at least 22 dynes/cm. One example is an ultraviolet irradiated polymer composition with 0.2 microns nominal pore size.

32 Claims, 6 Drawing Sheets

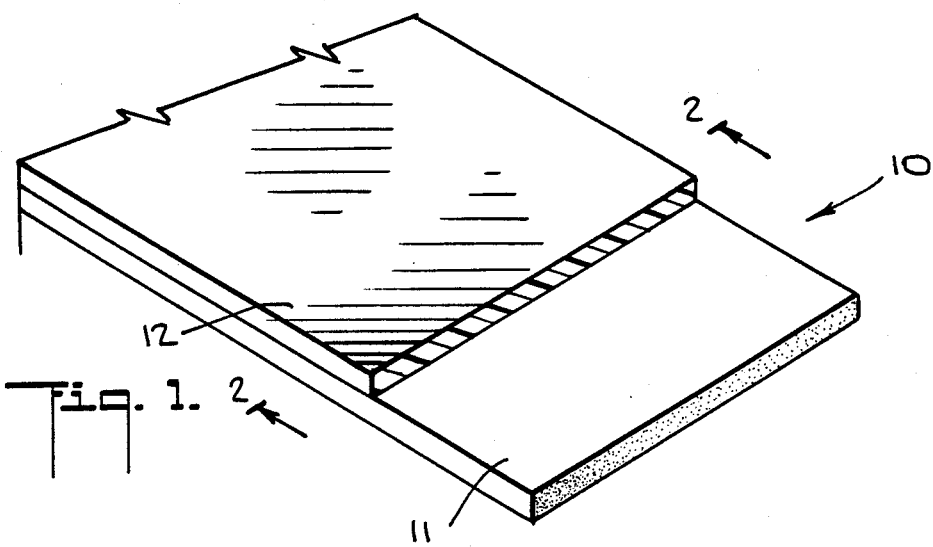
Fig. 1.
Fig. 2.
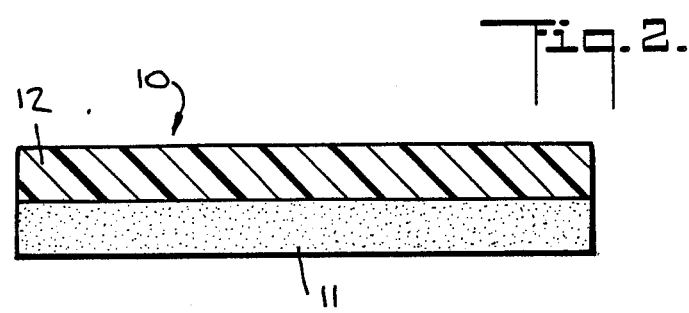
Fig. 7.
Fig. 8.
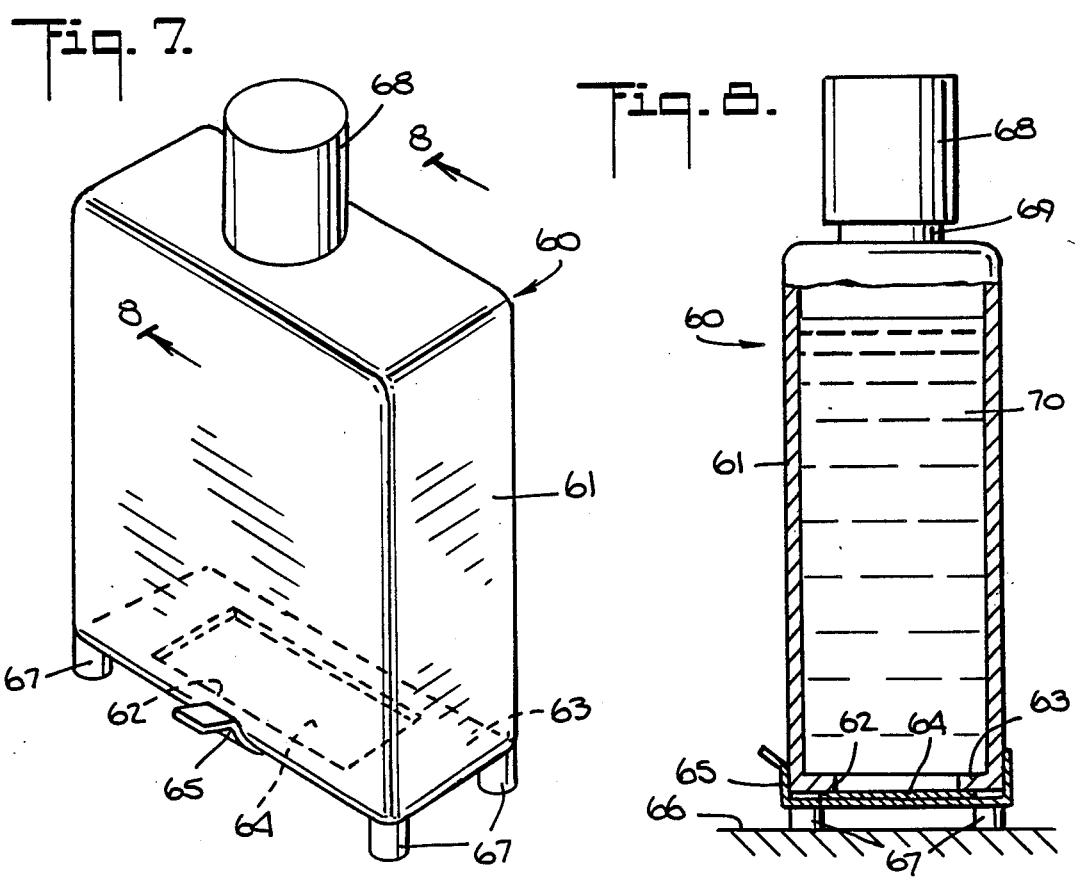

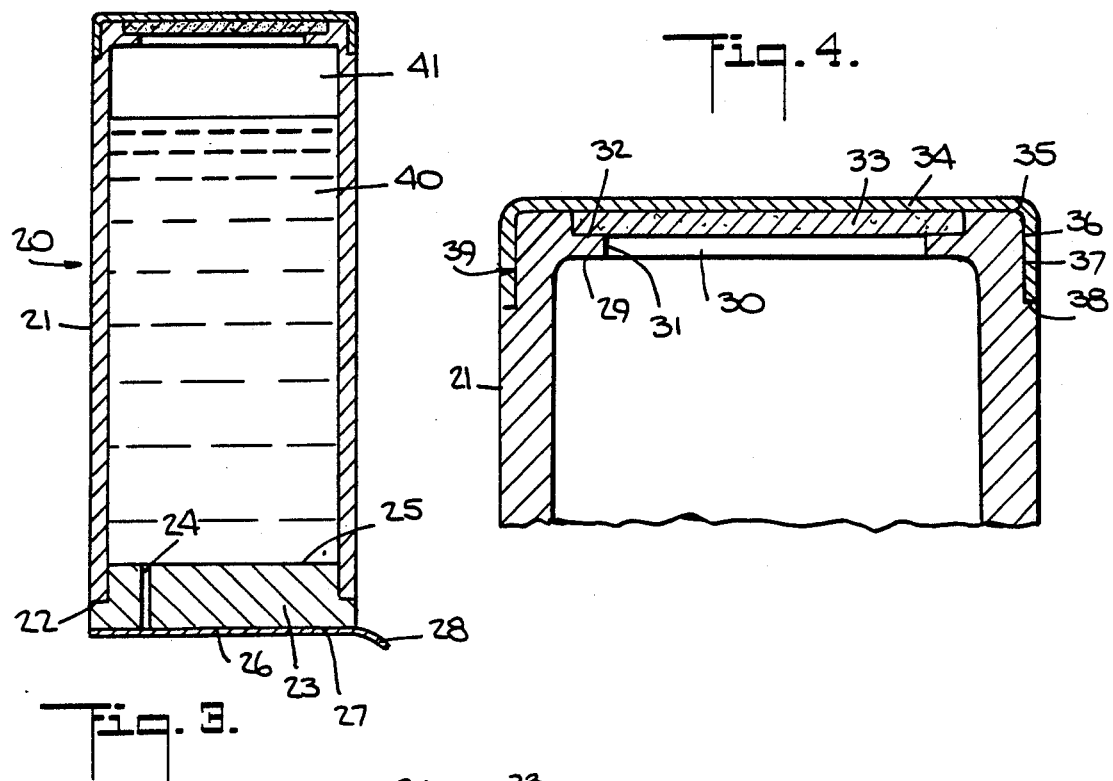
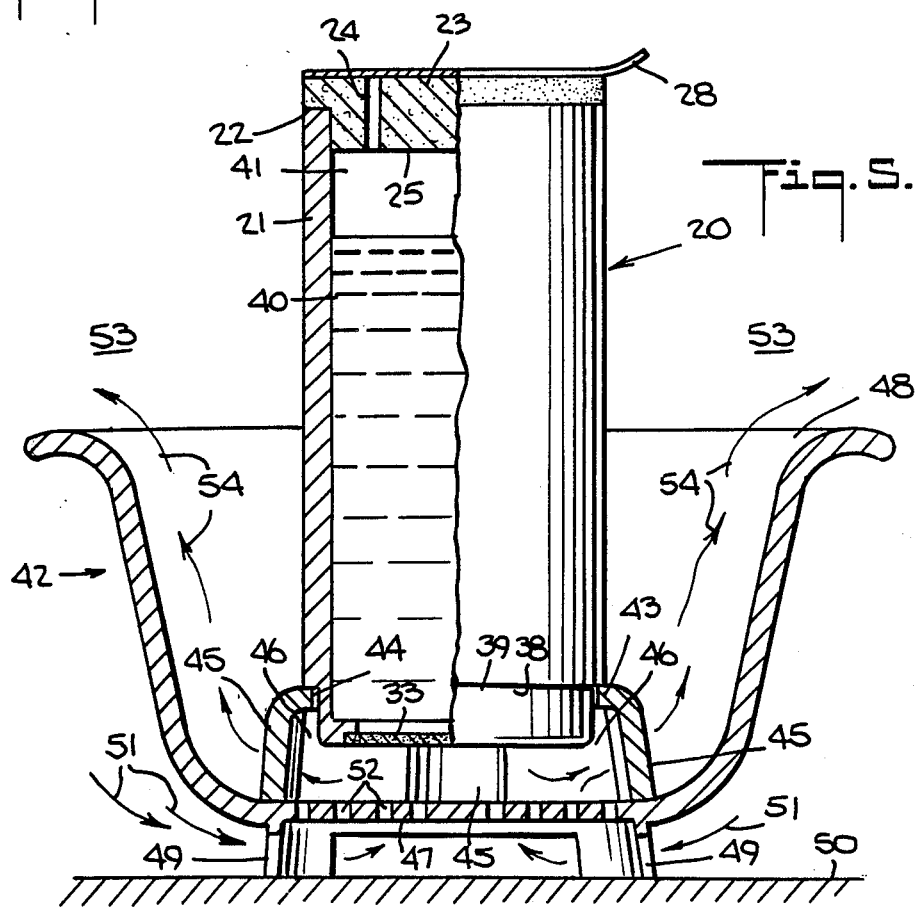

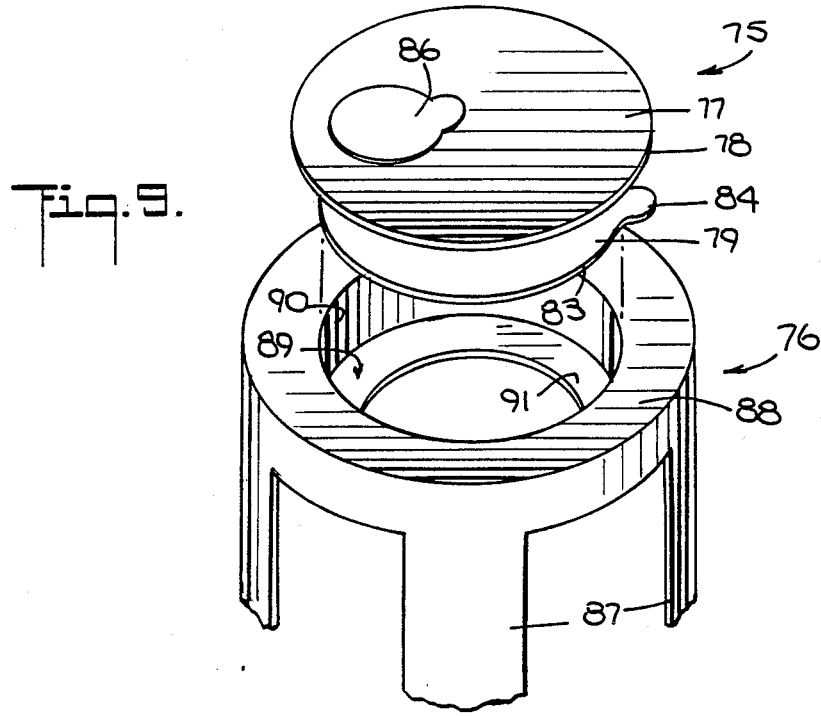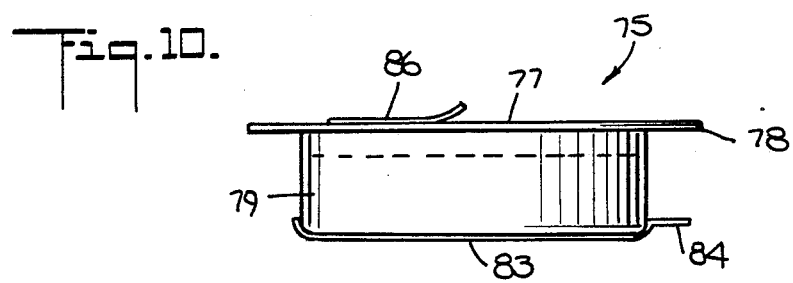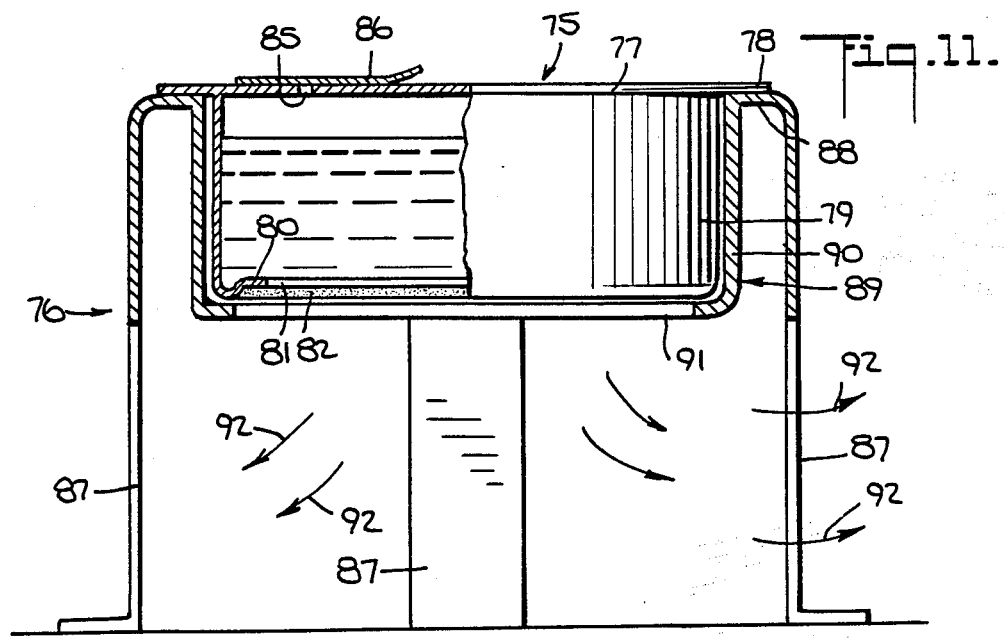

CONTAINER WITH MICROPOROUS MEMBRANE FOR DISPENSING VAPOR FROM VOLATILE LIQUID

BACKGROUND OF THE INVENTION

The present invention relates to apparatus for packaging and dispensing a volatile substance to be dispensed in a vapor phase. In particular, it relates to apparatus for dispensing air fresheners, aromatizing agents, deodorizers, odor maskents, insect repellents, animal repellents, pheromones and combinations thereof.

Numerous vapor releasing devices have been described in the literature and manufactured heretofore. In some, the vaporizable substance is incorporated in a solid carrier medium from which it gradually evaporates and enters the atmosphere once a protective wrap or enclosure is breached or removed. In others, the substance is packaged in liquid form and vaporized in some manner to discharge into the atmosphere. It is with this latter type that the present invention closely relates.

In particular, a type of room freshener is known wherein an aromatic liquid is packaged in a container provided with a wick immersed in the liquid and communicating with a porous member having a broad evaporation promoting surface. Unfortunately, the pores of the wicking material and the porous member tend to clog while the surface of the porous member tends to discolor rendering the device both less effective and unattractive. In addition, the presence of liquid on the exterior surface creates a number of problems since the liquid can be an irritant if carried to the eyes of an individual, the liquid can be gotten on clothes, and can otherwise cause undesirable soiling.

Certain of the prior art devices have employed microporous membranes. Thus in Van Loveren et al. U.S. Pat. No. 4,387,849 there is described a hollow container comprising a shell which is at least partially porous, containing an entrapped volatile substance. The substance is entrapped in a gel and is, in the alternative, a perfume composition, a deodorant composition, an air freshener composition, an insecticide composition, a herbicide composition, an odor masking composition, a pheromone composition, an animal repellent composition, or an insect repellent composition. The container containing the entrapped volatile substance ceases to discharge into the atmosphere when placed in an outer air-tight container. Said patent refers to various microporous polymers giving as examples a polypropylene and filler composition, a polyurethane and filler composition, a composition of polyvinyl alcohol and xanthan gum, and a cyclodextrin and activated silicate composition. The patent also mentions production of a microporous film by heating a mixture of synthetic thermoplastic polymer which may be a polymer or a copolymer of an ethylenically unsaturated monomer, condensation polymer, polyphenylene oxide or a blend thereof and a compatible liquid to a temperature and for a time sufficient to form a homogeneous solution, allowing the solution to assume a desired shape and cooling the solution to initiate liquid-liquid phase separation followed by cooling to solidify the film.

The Van Loveren patent also describes a number of structural embodiments. The embodiment illustrated in its FIGS. 5 and 7, for example, takes the form of a right circular cylinder with microporous walls and containing the fragrance bearing gel which cylinder is packaged in an outer vial provided with a screw cap top. While the entire side wall of the cylinder is illustrated as microporous, the patent states that not all of the side wall need be so fabricated. Instead, merely the upper third or the upper quarter or the lower quarter of the side wall or even the top or the bottom of the cylindrical container may be fabricated from microporous polymer, the remainder of the cylinder shell being fabricated using a transparent substance which is rigid or flexible or using a silicate or quartz glass.

Experience with all of the microporous membranes mentioned in the Van Loveren et al. patent indicates that a captivating medium such as the disclosed gels is essential to prevent the volatile substance from wetting the outer surface of the microporous membrane and even forming droplets on the outer surface. This can stain and damage anything that comes in contact with it.

SUMMARY OF THE INVENTION

With the foregoing as background it is an object of the present invention to provide apparatus for packaging and dispensing a volatile organic substance where the substance can be packaged in liquid form without the need of gels or sponges to hold it captive.

It is a further object to provide a vapor dispensing container which never becomes wet to the touch on its exterior surfaces yet efficiently emits vapors from a liquid charge maintained at atmospheric pressure.

In accordance with the present invention there is provided apparatus for packaging and dispensing a volatile substance stored in a liquid phase and dispensed in a vapor phase where the apparatus comprises a container for confining at atmospheric pressure and room temperature a quantity of a volatile substance that is liquid at atmospheric pressure and room temperature and has a surface tension in its liquid phase that is above a predetermined value. The container is formed by first and second wall portions, the first wall portion being essentially impervious to the substance and includes means for establishing communication between the interior of the container and the atmosphere when it is desired to dispense the substance. The second wall portion includes a microporous membrane having interior and exterior surfaces with the exterior surface exposable to the atmosphere surrounding the container. The membrane has an active structure formed from a material that lacks affinity for the substance which material has a critical surface tension that is below the predetermined value of surface tension mentioned above. The membrane has an air flow permeance such that when the exterior surface of the membrane is exposed to the atmosphere the substance is transported through the second portion and discharged into the atmosphere as a vapor while the exterior surface of the second portion remains dry to the touch.

BRIEF DESCRIPTION OF THE DRAWINGS

The invention will be better understood after reading the following detailed description of the presently preferred embodiment thereof with reference to the appended drawings in which:

FIG. 1 is a fragmentary perspective view with portions broken away of a microporous membrane for use in fabricating embodiments of the invention;

FIG. 2 is an enlarged transverse sectional view of the membrane shown in FIG. 1 taken along the line 2—2 in FIG. 1;

FIG. 3 is a vertical sectional view of a container for an aromatizing substance representing one embodiment of the present invention;

FIG. 4 is an enlarged fragmentary sectional view similar to FIG. 3 showing the microporous membrane and foil seal in greater detail;

FIG. 5 is a vertical sectional view of the container embodiment of FIG. 3 shown in dispensing orientation supported by a cup-shaped stand in spaced relation to a supporting table top or the like;

FIG. 7 is a perspective view of another embodiment of the invention where the overall container resembles a bottle but has a microporous membrane closing a portion of its bottom wall and has feet for maintaining the container bottom elevated above the supporting surface;

FIG. 8 is a vertical sectional view taken along the line 8—8 in FIG. 7;

FIG. 9 is an exploded perspective view of another embodiment having both a stand and a dispensing container, the latter resembling a disc;

FIG. 10 is a side elevational view of the container of FIG. 9;

FIG. 11 is a vertical sectional view of the embodiment of FIG. 9 showing details in the construction with the container in dispensing condition;

Throughout the drawings the same reference numerals are used to designate the same or similar parts.

DETAILED DESCRIPTION OF THE PRESENTLY PREFERRED EMBODIMENTS

Figure 6:
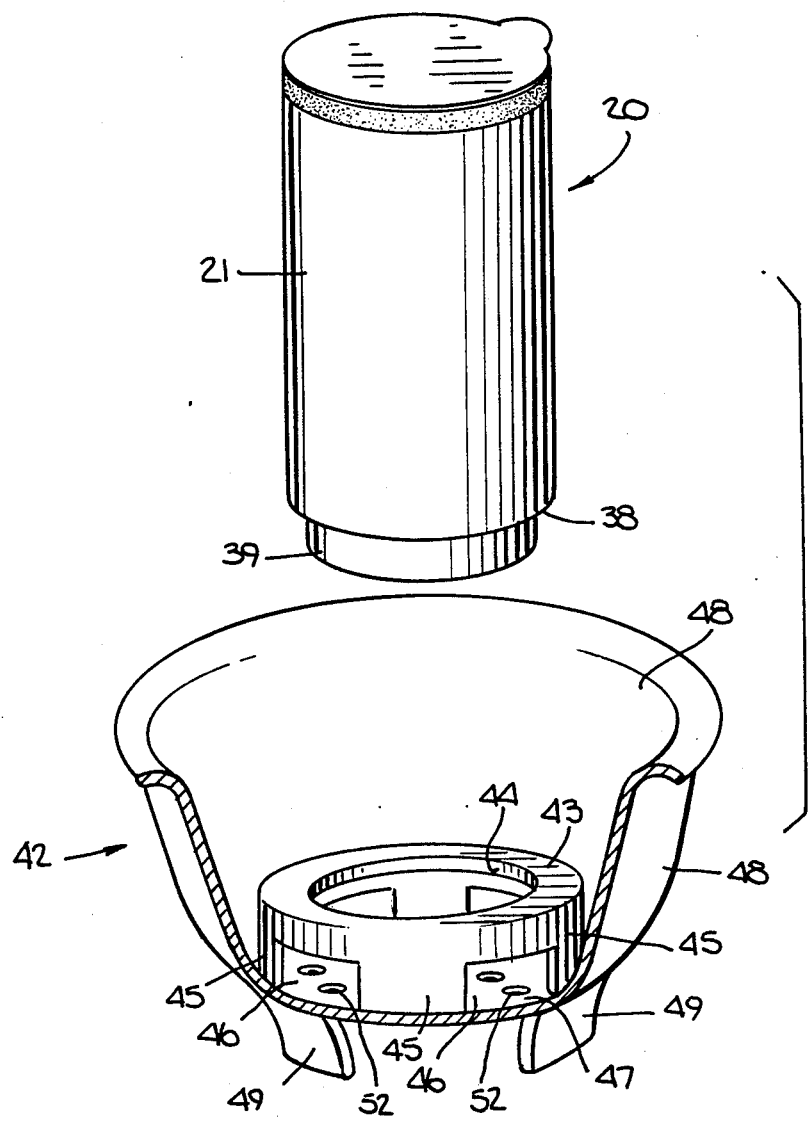
FIG. 6 s an exploded perspective view of the embodiment of FIGS. 3–5, with a portion broken away.

The present invention arises from the discovery that a certain type of microporous membrane, when placed in contact with liquid substances of the type used to provide aromatic vapors, will enable emission of the vapors of the substance while preventing passage of the liquid, at least to the extent that droplets do not reach the exposed surface of the membrane and the exposed surface remains dry to the touch. One such membrane is illustrated somewhat diagrammatically in FIGS. 1 and 2. As shown therein, the membrane is designated generally by the reference numeral 10, and consists essentially of a porous supporting substrate 11, and a coating layer of a microporous polymer 12.

A membrane with the foregoing construction that has been found satisfactory for the purposes of the present invention is manufactured by Gelman Sciences Technology Ltd. of Ann Arbor, Mich., and marketed under their "Sunbeam Process" trademark as "REPEL Microporous Membrane" Such membrane has a substrate 11 in the form of a nonwoven polyester sheet, while the layer 12 is formed from a thin film layer of a microporous polymer. According to the manufacturer, the membrane is produced using the process described in U.S. Pat. No. 4,466,931, issued Aug. 21, 1984, incorporated herein by reference. Said patent describes use of ultraviolet irradiation or the like for promoting polymerization of the resin. However, the production of the membrane does not constitute a part of the present invention and will not be described in further detail.

A sample membrane from Gelman Sciences was specified by the manufacturer as having a nominal pore size of 0.2 microns, a coating (i.e., the layer 12) weight of 23.6 gm/m$^2$, an air flow characteristic of 110 ml/min cm$^2$ at 80 cm H$_2$O, and a water break through pressure greater than 4.5 kg/cm$^2$. Another sample was specified as having a nominal pore size of 0.2 microns, a coating weight of 25 gm/m$^2$, an air flow characteristic of 100 ml/min cm$^2$ at 80 cm H$_2$O, a water break through pressure at least as great as 4 kg/cm$^2$ and a bubble point for kerosene of at least 2 atmospheres. Both samples were essentially solventphobic.

As a general requirement for the present invention, the active membrane layer 12 should be fabricated from a material that lacks affinity for the liquid substance whose vapor is to pass the membrane. In addition, the membrane material should have a critical surface tension that is no greater than 22 dynes/cm and preferably no greater than 20 dynes/cm. Consequently, so long as the surface tension of the liquid substance exceeds a 22 dynes/cm value, it will not wet the layer 12 and pass through as a liquid. As will appear below, the liquid substances generally have a surface tension characteristic of at least 22 dynes/cm.

The instant discovery enables production of an entire family of dispensers that serve as both the package for containing the liquid substance and the dispenser therefor. A few typical embodiments will now be described.

Reference should be had to FIGS. 3 to 6 wherein a liquid container 20 is shown as formed from a cylindrical bottle o vial 21 having an end 22 sealed with a cork stopper 23 or any other suitable capping structure. As best seen in FIGS. 3 and 5, the stopper 23 has a passage 24 passing completely through from the inner surface 25 to the outer surface 26. The purpose of passage 24 will be explained below. Also, a piece of impervious foil 27 is peelably adhesively secured over the surface 26 of stopper 23 to occlude passage 24. To facilitate removal of foil piece 27, it can be provided with a projecting tab 28.

The opposite end of the bottle 21 (best seen in FIG. 4) has an end wall 29 with an opening 30 bounded by radially inwardly directed flange 31 and counterbore 32. Closing the opening 30, set within the counterbore 32 and engaging flange 31, is a microporous membrane 33 constructed as discussed above with reference to FIGS. 1 and 2. The membrane 33 should be bonded to the walls of bottle 21 by any suitable adhesive inert to the liquids to be packaged in the container and compatible with the materials of both the bottle and membrane.

for sealing the container during storage and shipment until it is desired to dispense the container contents, another piece of impervious foil 34 is peelably adhesively applied over the entire surface of membrane 33, overlapping the top edge 35 and side wall 36 of the bottle into a ribbet 37 terminating in a shoulder 38, providing a reduced diameter head portion 39. While not shown, the foil 34 should be provided with an accessible tab extension to facilitate removal of the foil by the user when it is desired to dispense the contents.

As shown in FIGS. 3 and 5, the container 20 is filled with a liquid 40 except for a slight air space 41 to allow for expansion if the contents should become heated during storage. The components 21, 23, 27 and 34 must be constructed of suitable materials such that they are essentially impervious to the liquid substance 40 being packaged. During the time that foils 27 and 34 remain undisturbed, the container should be essentially hermetically sealed. However, when it is desired to dispense the liquid 40, for example a room freshener composition, the foils 27 and 34 are peeled off and the container 20 is placed inverted on a stand 42 as shown in FIG. 5 and 6.

The stand 42 is generally cup-shaped and has within the cup an encircling flange 43 with a central opening 44. The reduced diameter head 39 of the container 20 is inserted through opening 44 until shoulder 38 engages the upper surface of flange 43. The flange 43 is supported on a series of legs 43 between which are openings 46. Below flange 43 is an apertured bottom wall 47, having apertures 52, that merges into the upwardly gently sweeping cup-shape structure 48. Finally, a series of spaced legs 49 support the wall 47 spaced above a table top or other support surface 50.

As illustrated in FIG. 5, air is free to move in the direction of the arrows 51 entering between legs 49 and passing through wall 47 to waft vapor from microporous membrane 33 out through openings 46 into the cup 48 and then out to the surrounding space 53.

Before considering further embodiments of the invention, it will be helpful to have an understanding of the liquids that are to be used with the subject packaging. In essence, it has been found that any volatile liquid can be dispensed in the manner of the invention if its surface tension exceeds the critical surface tension of the material from which the microporous membrane is constructed. This assumes, of course, that the materials of the container and the liquid are compatible and mutually inert.

With the container 20 inverted as in FIG. 5 and the liquid head of liquid 40 acting on membrane 33, the outer exposed surface of membrane 33, after removal of foils 34 and 27, will remain dry to the touch, but vapor from the liquid, following the path of arrows 54, will discharge into the surrounding space 53. All of this occurs at room temperature and atmospheric pressure. The passage 24 in stopper 23 serves as a vacuum breaker establishing communication between the atmosphere and the space 41 when foil seal 27 is removed.

A typical room freshener or aromatizing composition for use with a container with a microporous window has the following composition:

| EXAMPLE I | |
|---|---|
| INGREDIENT | % BY WEIGHT |
| Fragrance** | 3.00 |
| Triton X 100* | 7.00 |
| SDA 39C Alcohol | 23.00 |
| Deionized Water | 67.00 |
| **FRAGRANCE | |
| INGREDIENT | PARTS BY WEIGHT |
| Terpineol | 448 |
| Hydroxy citronellal | 133 |
| Heliotropin | 160 |
| INGREDIENT | % BY WEIGHT |
| Phenylethyl alcohol | 50 |
| Benzyl Acetate | 82 |
| Anisaldehyde | 95 |
| Oil of cananga | 6 |
| Coumarin | 3 |
| Alpha ionone | 6 |
| Methyl jasmonate | 8 |
| 2,3-dimethyl-hydroquinone | 6 |
| p-methoxy acetophenone | 3 |
| Mixture of substituted isopropyl methyl | 35 |

| -continued | |
|---|---|
| cyclohexenones | |

*Octoxynol-9 (Rohm & Haas)

For a more detailed description of the composition and of other compositions, reference should be had to U.S. Pat. No. 4,400,311, incorporated herein by reference. In particular, said patent contains a description of the method of preparing the mixture of substituted isopropyl methyl cyclohexenones.

Figure 12:
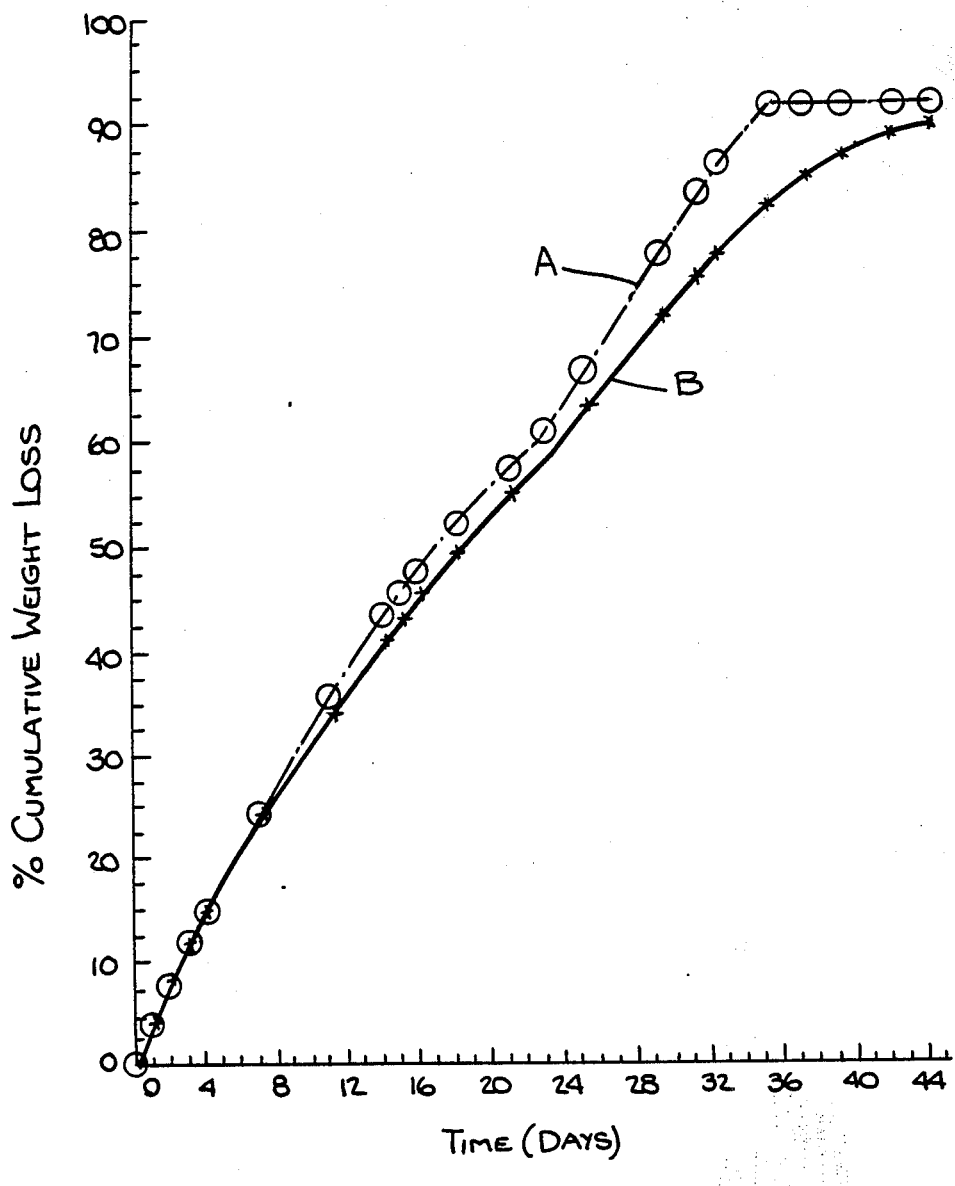
FIG. 12 is a graph comparing the evaporation rate of an exemplary volatile substance both in free communication with the atmosphere and through a typical membrane of the invention.

In order to determine the efficacy of the dispenser according to the present invention, data was obtained for the percent cumulative weight loss experienced by a given quantity of the volatile liquid: (a) when exposed directly to the atmosphere, and (b) when separated from the atmosphere by but in direct contact with a microporous membrane of the type described above. The results are plotted in FIG. 12 as curves A and B, respectively, from which it will be observed that there is very little difference in rate for at least 24 days, and that the rate remains steady until close to 90% has evaporated. Over the entire period of 44 days, the membrane remained dry to the touch.

Figure 13:
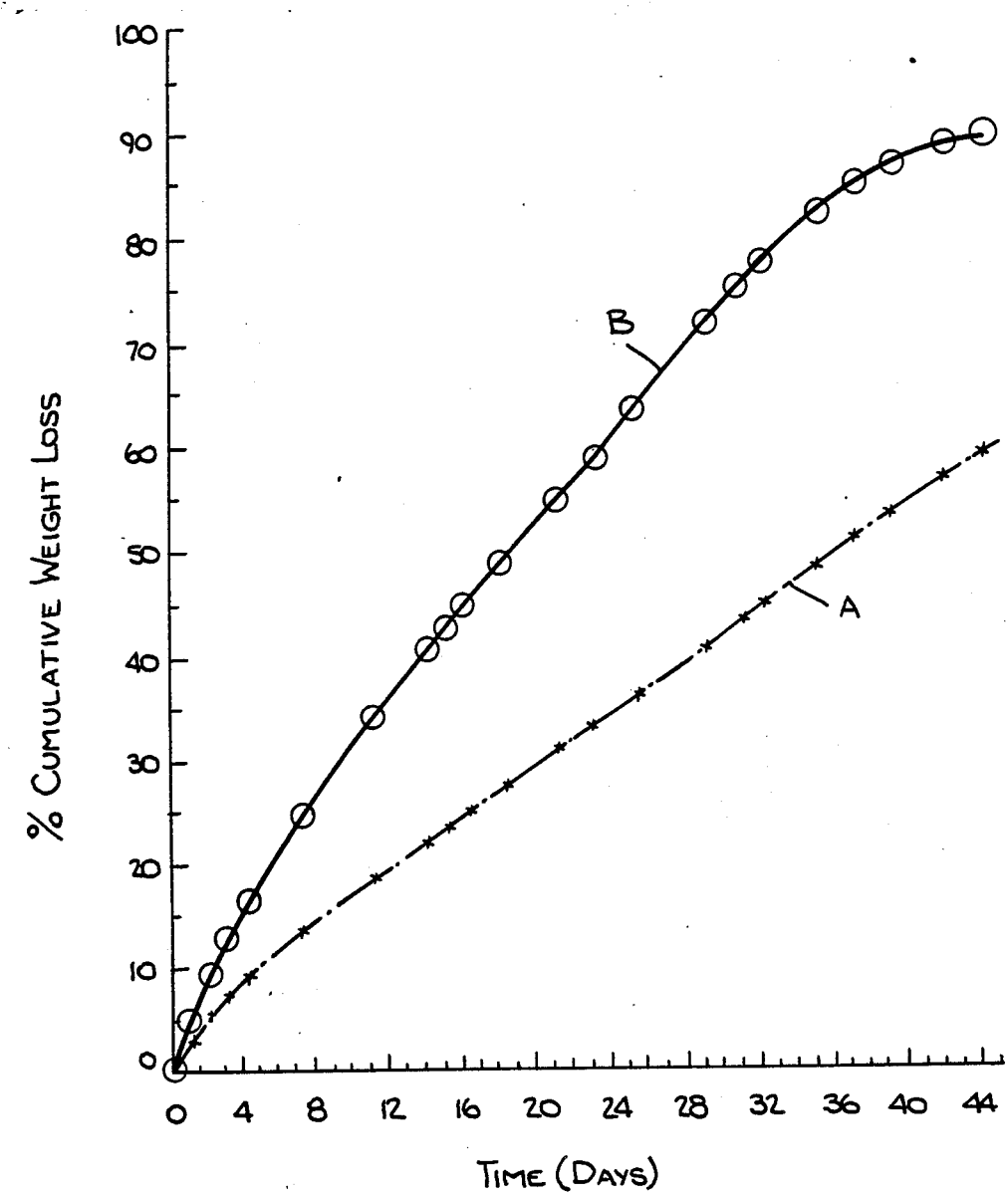
FIG. 13 is a graph illustrating the effect upon evaporative rate of change in surface area of the membrane.

Another experiment was performed to determine effect of membrane surface area upon percent cumulative weight loss, and the results are plotted in FIG. 13. Curve "A" was obtained with a membrane having a surface area of 7.9 cm$^2$ while curve "B" was obtained with a membrane having a surface area of 15.6 cm$^2$. The rate of weight loss was approximately 0.37 g/cm$^2$/day, the same for each sample, showing that the surface area affects the discharge rate in a linear manner.

Turning to FIGS. 7 and 8, there is illustrated another embodiment of the invention wherein the package and stand are integrated into a single structure. The container, designated generally by the reference numeral 60 consists of a bottle 61 with an opening 62 in its bottom 63 covered by a microporous membrane "window" 64, sealed until use by an overlying foil layer 65. To space the window 64 above the table or other supporting surface 66, the bottle 61 is furnished with feet 67. A conventional screw cap 68 takes the place of seal 27 of FIG. 3 and caps a vent passage (not shown) in bottle neck 69. Operation of the dispenser of FIGS. 7 and 8 to dispense liquid 70 should be self-evident. The cap 68 is removed along with foil 65 and vapors will commence to enter the surrounding atmosphere from membrane 64.

FIGS. 9 to 11 illustrate another embodiment, in two parts, consisting of a container 75 and a stand 76. The container 75 has a top wall 77, a radially extending flange 78, and a cylindrical cup portion 79. The cup portion 79 has a bottom the central portion of which, 80, is slightly recessed, apertured at 81, and covered by porous membrane 82. The extent by which the portion 80 is recessed is determined by the thickness of the membrane 82 such that the entire bottom is generally smooth and readily sealed by the peelable foil 83 with tab 84. A vent opening 85 is provided in top wall 87 and sealed by a removable foil element 86.

The stand 76 has a plurality of feet 87 supporting an annular seat 88 which engages the flange 78 on container 75, and a receiving well 89 having a side wall 90 and an apertured bottom wall 91. Air passing beneath the well 89 as shown by arrows 92 between feet 87 can waft vapor from the membrane 82 when the container 75 is activated by removing foils 83 and 86 and placing the container in well 89 as shown in FIG. 11. The operation is the same as with the previously described embodiments.

The foregoing description describes the various containers as having a base element 21, 61, or 77 and 79 defined by wall portions that are essentially impervious to the liquid substance to be packaged therein. In addition the material of which such wall portions are constructed must not adversely react with the liquid substance. Obviously, it should have sufficient strength and rigidity to function as required. It is believed that selection of the appropriate materials is well within the knowledge and scope of those skilled in the relevant art. Among suitable materials are glass, certain metals, and non-porous plastic such as polyethylene.

The window or second wall portion in each embodiment is constructed of a microporous membrane with the requirement that the nominal pore size fall within the range of 0.1 to 5 microns with a 0.2 micron nominal pore size being presently preferred. Satisfactory membranes have a nominal total thickness of 30 to 600 microns with a substrate nominal thickness of 15 to 300 microns and a microporous layer nominal thickness of 15 to 300 microns. While the microporous membrane may consist of an active porous layer on a porous substrate where the porous substrate provides mechanical support for the active layer as described in U.S. Pat. No. 4,466,931, the porous substrate can be omitted if the active layer is of sufficient thickness to be self supporting.

The volatile liquid substances that can be packaged and dispensed using the embodiments described herein are those ranging in surface tension from 22 to 72 dynes/cm and encompass substantially all volatile perfumes, air freshener compositions, deodorizers, animal repellents, insect repellents, and pheromone compositions and combinations thereof.

The microporous membranes must be fabricated from a material that has a critical surface tension that is below the surface tension of the liquid. With the liquid surface tensions ranging from 22 to 72 dynes/cm, the membrane critical surface tension should be below 22 dynes/cm and preferably no greater than 20 dynes/cm. At present it is preferred to select the membrane active material from the group consisting essentially of poly fluoro compounds, polyimines, polybutadienes, copolymers of fluoro vinyl compounds with ethylene, and copolymers of fluoro vinyl compounds with acrylates.

While the embodiment of FIGS. 3 to 6 has been described as having a cork plug or cap 23, it should be apparent that any suitable closure with a vent passage can be used. The cork cap 23, however, was conceived as a convenient removable stopper whereby the container 20 can be filled rapidly with the desired liquid and then capped.

As used throughout this specification, critical surface tension, applied to solid materials, serves to define the wettability of a surface of the solid by noting the lowest surface tension a liquid can have and still exhibit a contact angle greater than zero degrees on that solid. For a discussion of this constant, reference can be had to the section entitled "Critical Surface Tensions of Polymers" by E. G. Shafrin appearing in *Polymer Handbook*, 2nd ed., Brandrup and Immergut eds., published by Wiley Interscience, 1975, p. III-221.

Having described the present invention with reference to the presently preferred embodiments thereof, it should be apparent to those skilled in the subject art that various changes in construction can be introduced without departing from the true spirit of the invention as defined in the appended claims.

What is claimed is:

1. Apparatus for packaging and dispensing a volatile substance stored in a liquid phase and dispensed in a vapor phase, said apparatus comprising a container for confining at atmospheric pressure and room temperature a quantity of a volatile substance that is liquid at atmospheric pressure and room temperature and has a surface tension in its liquid phase that is above a predetermined value, said container being formed by first and second wall portions, said first wall portion being essentially impervious to said substance and including means for establishing communication between the interior of the container and the atmosphere when it is desired to dispense said substance, said second wall portion including a microporous membrane having interior and exterior surfaces with the exterior surface exposable to the atmosphere surrounding said container, said membrane having an active structure formed from a material that lacks affinity for said substance and has a critical surface tension that is below said predetermined value, said membrane having an air flow permeance such that when said exterior surface is exposed to the atmosphere and said interior surface is in contact with the liquid, said substance is transported through said second portion and discharged into the atmosphere as a vapor while said exterior surface of said second portion remains dry to the touch.

2. Apparatus according to claim 1, wherein said predetermined value of surface tension of said liquid is at least 22 dynes/cm.

3. Apparatus according to claim 2, wherein said surface tension of said liquid is in the range of 22 to 72 dynes/cm.

4. Apparatus according to claim 3, wherein said material of said membrane has a critical surface tension that is less than 22 dynes/cm.

5. Apparatus according to claim 4, wherein said of said membrane is a fluorocarbon resin.

6. Apparatus according to claim 5, wherein said membrane has a nominal pore size of about 0.2 microns and an air transmission rate ranging from about 100 to about 110 ml/min/cm$^2$ at 80 cm water column pressure.

7. Apparatus according to claim 4, wherein said active structure of said membrane comprises a microporous body formed from a material selected from the group consisting essentially of poly fluoro compounds, polyimines, polybutadienes, copolymers of fluoro vinyl compounds with ethylene, and copolymers of fluoro vinyl compounds with acrylates.

8. Apparatus according to claim 3, wherein said active structure of said membrane comprises a microporous body formed from a material selected from the group consisting essentially of poly fluoro compounds, polyimines, polybutadienes, copolymers of fluoro vinyl compounds with ethylene, and copolymers of fluoro vinyl compound with acrylates.

9. Apparatus according to claim 3, wherein said active structure is a microporous membrane through which only the vapor phase of said substance can pass where said substance is a volatile composition selected from the group consisting of perfume, air freshening, deodorizing, animal repellent, insect repellent, and pheromone compositions and combinations thereof.

10. Apparatus according to claim 9, wherein said material of said active structure is a fluorocarbon resin.

11. Apparatus according to claim 2, wherein said material of said membrane has a critical surface tension that is less than 22 dynes/cm.

12. Apparatus according to claim 11, wherein said material of said membrane is a fluorocarbon resin.

13. Apparatus according to claim 12, wherein said membrane has a nominal pore size of about 0.2 microns and an air transmission rate ranging from about 100 to about 110 ml/min/cm$^2$ at 80 cm water column pressure.

14. Apparatus according to claim 12, wherein said membrane comprises a support substrate, and said active structure comprises a microporous polymer layer supported on said substrate.

15. Apparatus according to claim 11 wherein said active structure of said membrane comprises a microporous body formed from a material selected from the group consisting essentially of poly fluoro compounds, polyimines, polybutadienes, copolymers of fluoro vinyl compounds with ethylene, and copolymers of fluoro vinyl compounds with acrylates.

16. Apparatus according to claim 11, wherein said active structure is a microporous membrane through which only the vapor phase of said substance can pass where said substance is a volatile composition selected from the group consisting of perfume, air freshening, deodorizing, animal repellent, insect repellent, and pheromone compositions and combinations thereof.

17. Apparatus according to claim 1, wherein said membrane comprises a support substrate, and said active structure comprises a microporous polymer layer supported on said substrate.

18. Apparatus according to claim 17, wherein said microporous polymer comprises a material selected from the group consisting essentially of poly fluoro compounds, polyimines, polybutadienes, copolymers of fluoro vinyl compounds with ethylene, and copolymers of fluoro vinyl compounds with acrylates.

19. Apparatus according to claim 1, wherein said active structure of said membrane comprises a microporous body formed from a material selected from the group consisting essentially of poly fluoro compounds, polyimines, polybutadienes, copolymers of fluoro vinyl compounds with ethylene, and copolymers of fluoro vinyl compounds with acrylates.

20. Apparatus according to claim 1, wherein said active structure is a microporous membrane through which only the vapor phase of said substance can pass where said substance is a volatile composition selected from the group consisting of perfume, air freshening, deodorizing, animal repellent, insect repellent, and pheromone compositions and combinations thereof.

21. Apparatus according to claim 20, wherein said material of said active structure is a fluorocarbon resin.

22. Apparatus according to claim 1, wherein said substance is an aromatizing composition.

23. Apparatus according to claim 1, wherein said second wall portion is disposed relative to said first wall portion such that when said container is in dispensing position elevated above a supporting surface said second portion is directed downwardly but spaced from said supporting surface and said liquid substance is in contact with and above said second portion, and said means for establishing communication between the interior of said container and the atmosphere is located, when the container is in dispensing position, at a point above said liquid substance to function as a vacuum breaker.

24. Apparatus according to claim 23, wherein said vacuum breaker means comprises a vent passage formed in a part of said first wall portion, and means for sealing off said vent passage prior to dispensing of said substance which means is defeatable by the user of the apparatus when dispensing of said substance is desired.

25. Apparatus according to claim 24, wherein means are provided for sealing off said exterior surface of said membrane from the atmosphere until dispensing of said substance is desired which means is defeatable by the user of the apparatus for enabling dispensing of said substance.

26. Apparatus according to claim 25, wherein said sealing means comprise pieces of peelable foil adhesively secured over the vent passage and membrane, respectively.

27. Apparatus according to claims 24, wherein said container is in the form of a bottle with a threaded neck, said vent passage passes through said bottle neck, and a screw cap threadedly engaged with said bottle neck, seals said vent passage until dispensing of said substance is desired.

28. Apparatus according to claim 27, wherein said bottle has at least one projection from its bottom to support said bottle upon a substantially flat surface with said bottom elevated above said flat surface, and said second portion of said wall is located in said bottom of said bottle.

29. Apparatus according to claim 23, wherein means are provided for sealing off said exterior surface of said membrane from the atmosphere until dispensing of said substance is desired which means is defeatable by the user of the apparatus for enabling dispensing of said substance.

30. Apparatus according to claim 23, wherein said means for supporting said container comprises a stand with means for receiving said container and supporting it spaced above a support surface with said membrane proximate said support surface and with space through which the surrounding atmosphere can move freely wafting over said exterior surface of said membrane picking up said substance vapor.

31. Apparatus according to claim 30, wherein said stand comprises a plurality of legs dependently disposed about an integral framework where the framework has an apertured section for locating and supporting said container with said membrane proximate said apertured section and the rest of said container above said membrane.

32. Apparatus according to claim 31, wherein said membrane comprises a fluorocarbon hydrophobic membrane.

* * * * *

UNITED STATES PATENT AND TRADEMARK OFFICE
CERTIFICATE OF CORRECTION

PATENT NO. : 4,917,301
DATED : April 17, 1990
INVENTOR(S) : MARINA A. MUNTEANU

It is certified that error appears in the above-identified patent and that said Letters Patent is hereby corrected as shown below:

Col. 3, l. 11, should read "Fig. 6 is an exploded"

Col 4, l. 31, should read "bottle or vial"

Col. 4, l. 51, should read "For sealing the"

Col. 4, l. 56, should read "into a rabbet 37"

Claim 5, l. 1, after "said" and before "of" insert --material--.

Claim 15, l. 1, insert a comma (,) after "claim 11"

Claim 27, l. 4, after "cap" change the period (.) to a comma --(,)--

Signed and Sealed this

Thirtieth Day of July, 1991

Attest:

HARRY F. MANBECK, JR.

*Attesting Officer*     *Commissioner of Patents and Trademarks*